(12) United States Patent
Panek et al.

(10) Patent No.: US 10,451,226 B2
(45) Date of Patent: Oct. 22, 2019

(54) MODULAR LED LINE LIGHT

(71) Applicant: ProPhotonix Limited, Salem, NH (US)

(72) Inventors: Peter Panek, Douglas (IE); John Sexton, Cork (IE); Kieran Lynch, Douglas (IE); John Brett, Cork (IE); Jan Kievits, Cork (IE)

(73) Assignee: ProPhotonix Limited, Salem, NH (US)

( * ) Notice: Subject to any disclaimer, the term of this patent is extended or adjusted under 35 U.S.C. 154(b) by 409 days.

(21) Appl. No.: 15/264,769

(22) Filed: Sep. 14, 2016

(65) Prior Publication Data

US 2017/0074471 A1 Mar. 16, 2017

Related U.S. Application Data

(60) Provisional application No. 62/218,397, filed on Sep. 14, 2015.

(51) Int. Cl.
| | |
|---|---|
| *F21V 23/06* | (2006.01) |
| *F21V 21/005* | (2006.01) |
| *F21V 5/00* | (2018.01) |
| *F21V 23/00* | (2015.01) |
| *F21V 5/04* | (2006.01) |
| *F21S 4/28* | (2016.01) |
| *H05B 33/08* | (2006.01) |

(Continued)

(52) U.S. Cl.
CPC .............. *F21S 2/005* (2013.01); *F21S 4/28* (2016.01); *F21V 5/004* (2013.01); *F21V 5/007* (2013.01); *F21V 5/04* (2013.01); *F21V 15/01* (2013.01); *F21V 17/12* (2013.01); *F21V 21/005* (2013.01); *F21V 23/003* (2013.01); *F21V 23/02* (2013.01); *F21V 23/06* (2013.01); *F21V 29/58* (2015.01); *G05B 19/042* (2013.01); *H05B 33/0845* (2013.01); *F21Y 2103/10* (2016.08); *F21Y 2115/10* (2016.08)

(58) Field of Classification Search
None
See application file for complete search history.

(56) References Cited

U.S. PATENT DOCUMENTS

| | | |
|---|---|---|
| 5,059,871 A | 10/1991 | Pearlman et al. |
| 5,523,384 A | 6/1996 | Jewell et al. |

(Continued)

FOREIGN PATENT DOCUMENTS

WO  WO 2014/064576  5/2014

*Primary Examiner* — Joseph L Williams
*Assistant Examiner* — Jacob R Stern
(74) *Attorney, Agent, or Firm* — Pandiscio & Pandiscio

(57) ABSTRACT

A modular LED line light, the modular LED line light comprising: at least one line light module, the at least one line light module comprising: a U-shaped body comprising a base and two opposing side walls extending from the base, the base comprising an interior surface and an exterior surface; at least one LED array disposed on the interior surface of the U-shaped body; a rail for receiving the at least one line light module, the rail comprising a first surface and a second surface, wherein the first surface is configured to receive the exterior surface of the base of the U-shaped body of the at least one light module; and a cooling tube for receiving a cooling fluid for removing heat from the at least one line light module, the cooling tube being disposed between the exterior surface of the base of the U-shaped body and the first surface of the rail.

27 Claims, 17 Drawing Sheets

Side view of modular light unit showing optical lens configuration

(51) Int. Cl.
*F21S 2/00* (2016.01)
*F21V 17/12* (2006.01)
*F21V 29/58* (2015.01)
*F21V 23/02* (2006.01)
*F21V 15/01* (2006.01)
*G05B 19/042* (2006.01)
*F21Y 115/10* (2016.01)
*F21Y 103/10* (2016.01)

(56) References Cited

U.S. PATENT DOCUMENTS

| | | |
|---|---|---|
| 5,990,802 A | 11/1999 | Maskeny |
| 6,239,975 B1 | 5/2001 | Otis |
| 6,659,623 B2 | 12/2003 | Friend |
| 6,827,475 B2 | 12/2004 | Vetorino et al. |
| 6,880,952 B2 | 4/2005 | Kiraly et al. |
| 7,071,908 B2 | 7/2006 | Guttag et al. |
| 7,296,912 B2 | 11/2007 | Beauchamp |
| 7,317,288 B2 | 1/2008 | Lin |
| 7,458,705 B2 | 12/2008 | Chiba et al. |
| 7,473,020 B2 | 1/2009 | Pickering |
| 8,002,443 B2 | 8/2011 | Shin et al. |
| 8,079,731 B2 | 12/2011 | Lynch et al. |
| 8,154,223 B2 | 4/2012 | Hsu et al. |
| 8,179,037 B2 | 5/2012 | Chan et al. |
| 8,237,372 B2 | 8/2012 | Hoogzaad et al. |
| 8,421,365 B2 | 4/2013 | Kong et al. |
| 8,462,292 B2 | 6/2013 | Parker et al. |
| 8,487,547 B2 | 7/2013 | Godbole |
| 8,513,904 B2 | 8/2013 | Weng |
| 8,618,738 B2 | 12/2013 | Wen et al. |
| 8,979,338 B2 | 3/2015 | Joseph |
| 2005/0063181 A1 | 3/2005 | Chiba et al. |
| 2007/0063338 A1 | 3/2007 | Chang et al. |
| 2008/0180414 A1 | 7/2008 | Fung et al. |
| 2012/0033431 A1* | 2/2012 | Martinez ............... F21V 15/013 362/294 |
| 2012/0223649 A1 | 9/2012 | Saes et al. |
| 2014/0115302 A1 | 4/2014 | Higham et al. |
| 2014/0159598 A1 | 6/2014 | Boezen |
| 2014/0253562 A1 | 9/2014 | Yaras |
| 2014/0268728 A1 | 9/2014 | Hussell et al. |
| 2014/0333859 A1 | 11/2014 | Zhang et al. |
| 2015/0198321 A1 | 7/2015 | Druchinin |

* cited by examiner

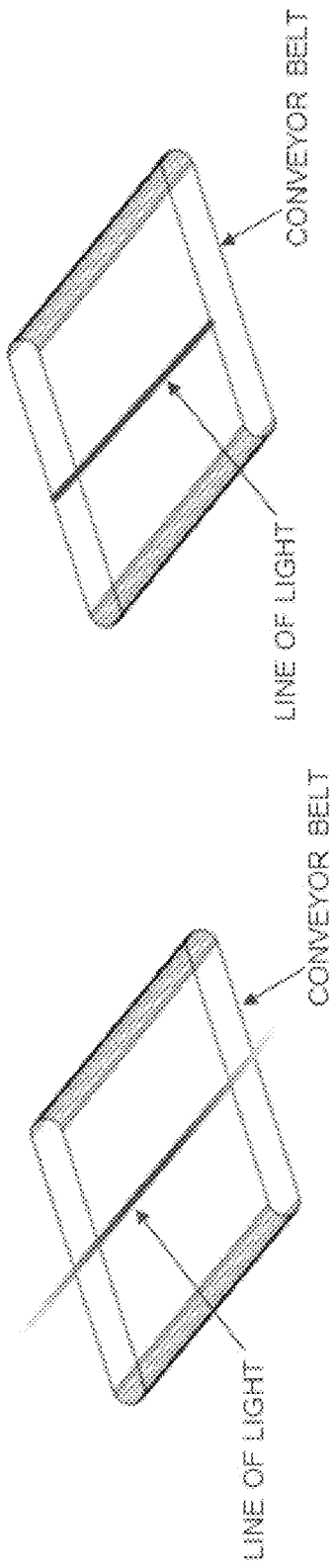

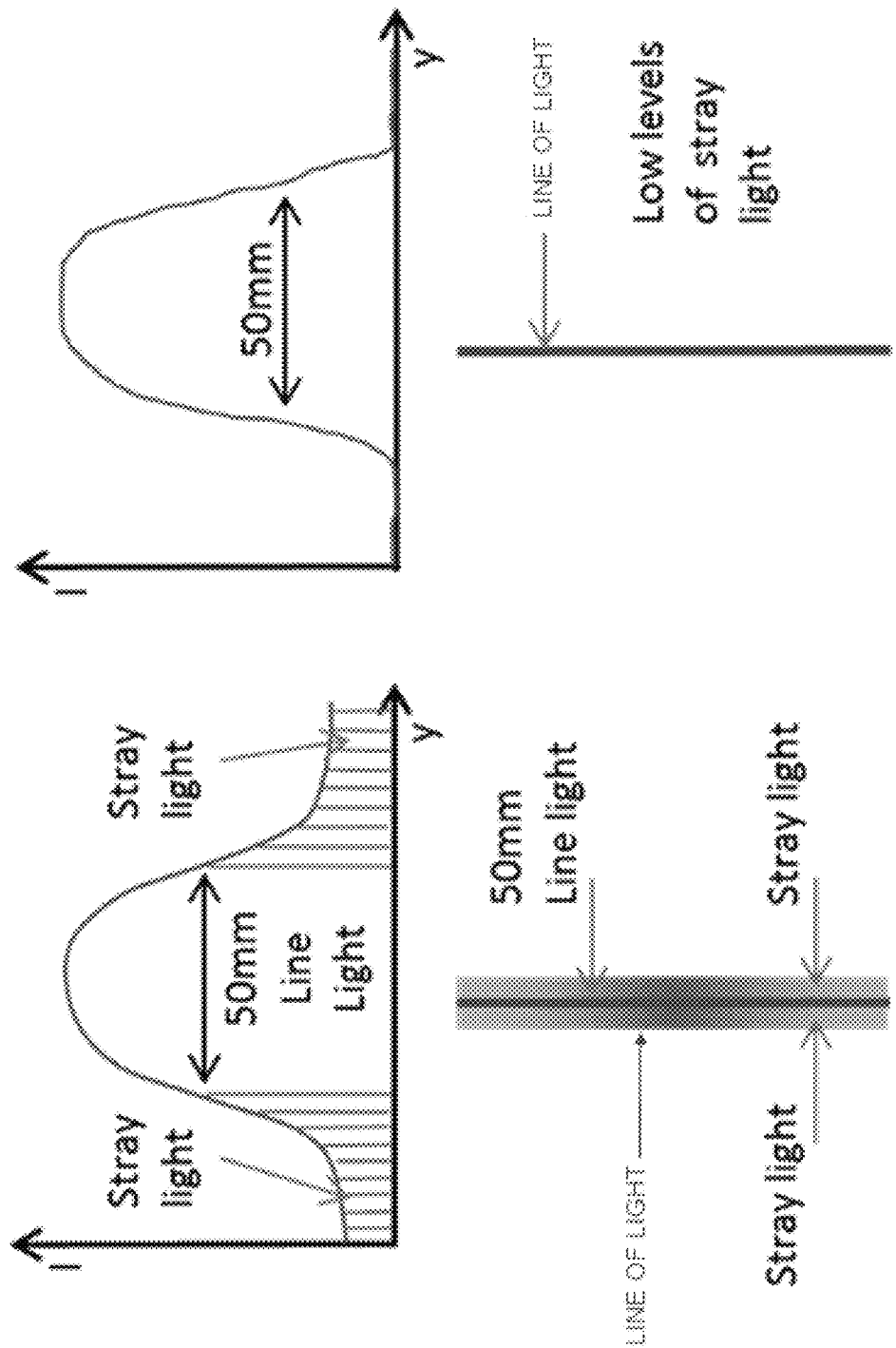

Front-on view of module mounting rail, a u-shaped cooling tube and an individual modular light unit.

Exploded view of the mounting rail, a u-shaped cooling tube and an individual modular light units.

Side-view of the line light showing how the mounting rail, a u-shaped cooling tube and modular light Cut-through of the line light showing how the mounting rail, a u-shaped cooling tube and modular light.

Side view of modular light unit showing optical lens configuration

Electronics shown on the outside of the line light

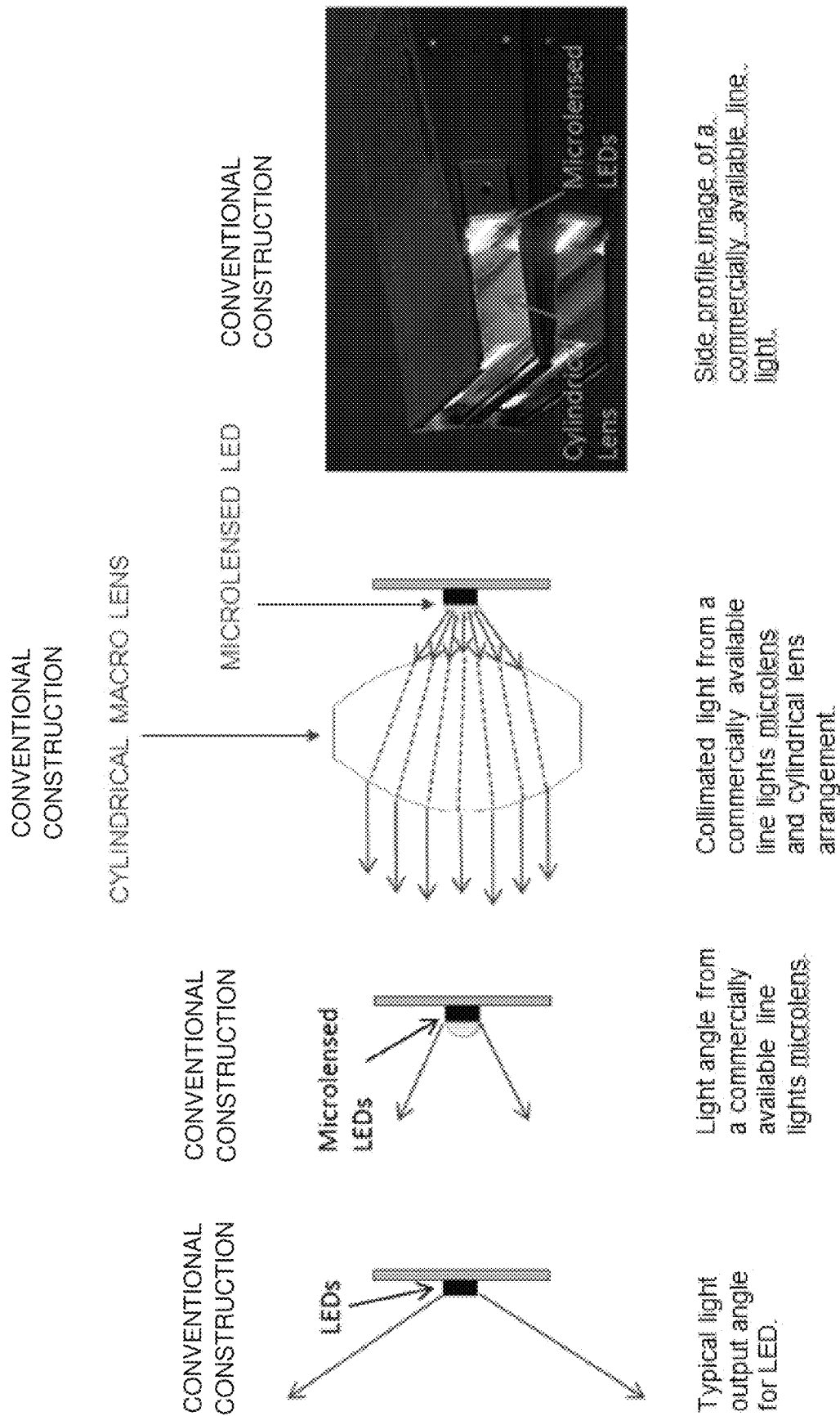
FIG. 15 Typical light output angle for LED.
FIG. 16 Light angle from a commercially available line lights microlens.
FIG. 17 Collimated light from a commercially available line lights microlens and cylindrical lens arrangement.
FIG. 18 Side profile image of a commercially available line light.

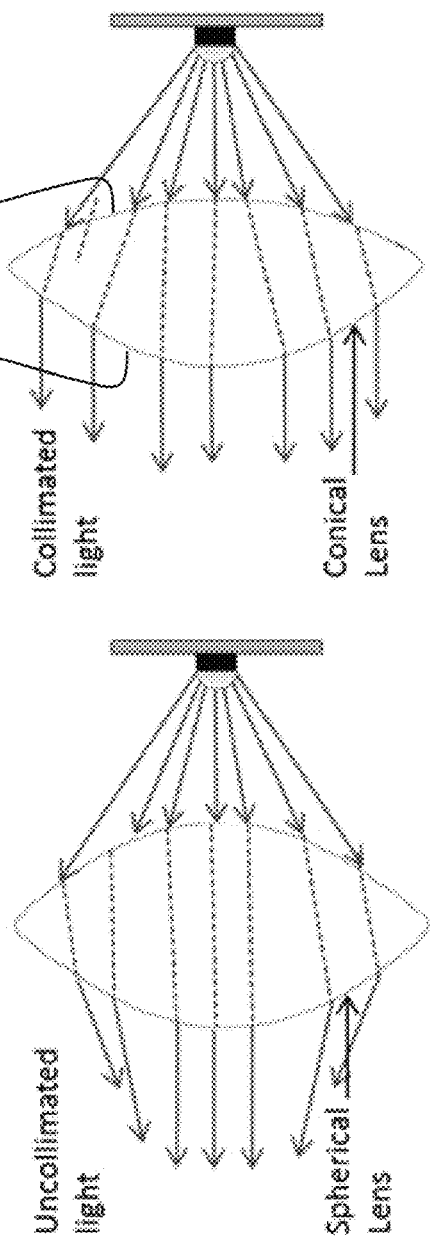

FIG. 19 Optical diagram of a line light showing the commercially available line lights. cylindrical lens where the distance between the two lenses is widened to work wider working distances.

FIG. 20 Optical diagram of the inventions custom lens where the distance between the two lenses is widened to produce a uniform collimated line to work at the required working distances.

FIG. 21 Side profile image of the inventions line light.

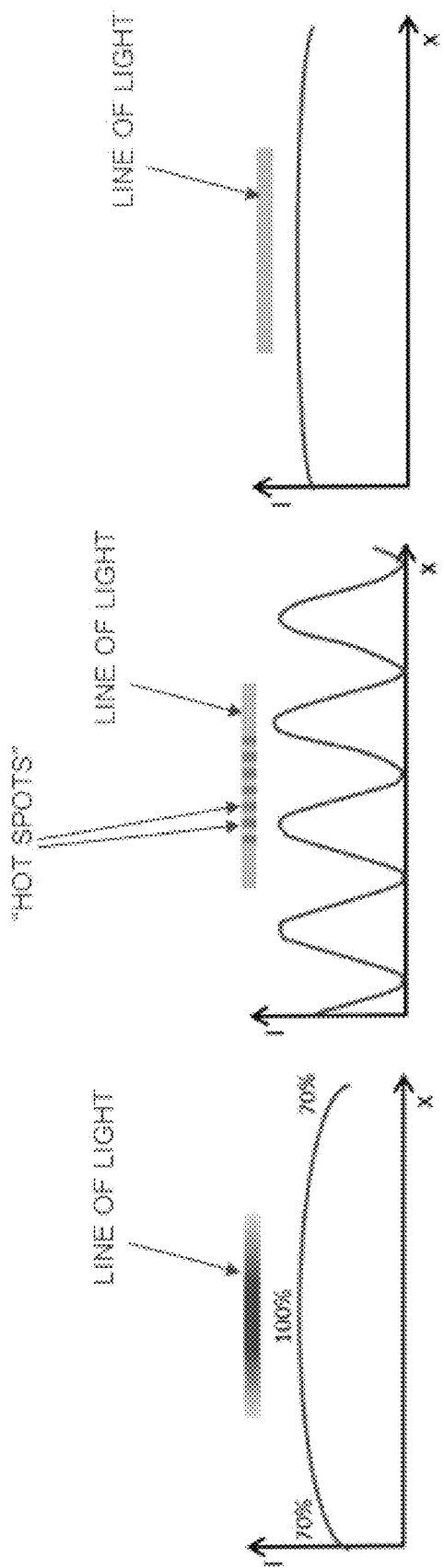

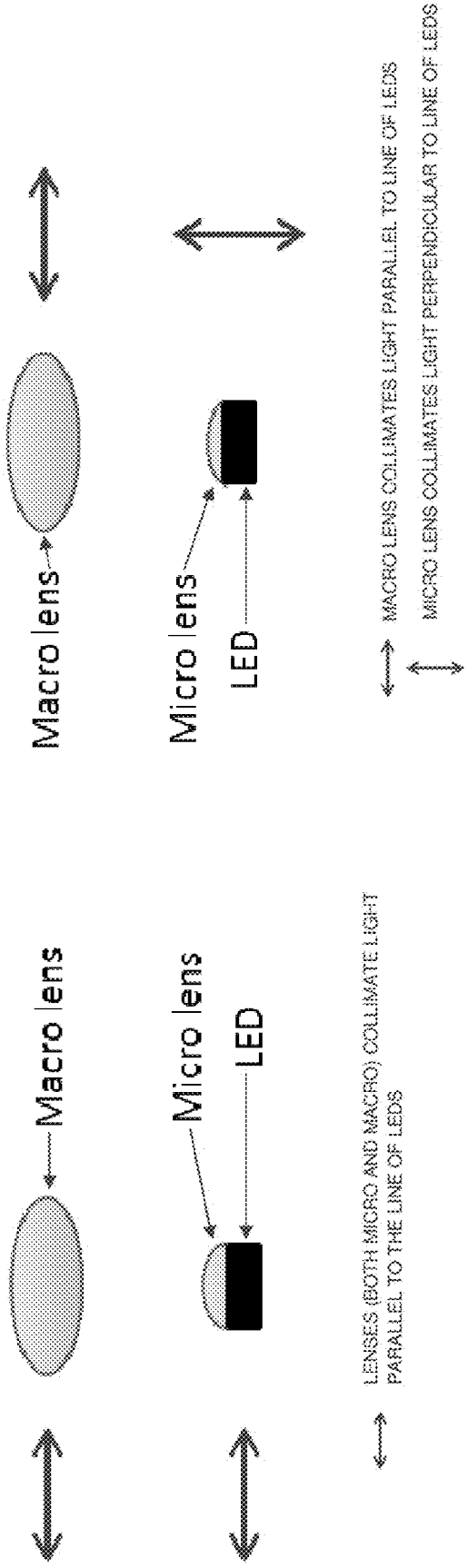

Bus bar with clips.

Bus bar integrated into the PCB

Manufacturer Specified Chip layout

Invention chip layout

MODULAR LED LINE LIGHT

REFERENCE TO PENDING PRIOR PATENT APPLICATION

This patent application claims benefit of prior U.S. Provisional Patent Application Ser. No. 62/218,397, filed Sep. 14, 2015 by ProPhotonix Limited and Peter Panek et al. for MODULAR LED LINE LIGHT, which patent application is hereby incorporated herein by reference.

FIELD OF THE INVENTION

This invention relates to lighting devices in general, and more particularly to a novel modular LED line light.

BACKGROUND OF THE INVENTION

Machine vision refers to methods and apparatus that are used to provide imaging-based automatic inspection and analysis for applications such as automatic inspection, process control and robot guidance in industry. Employing the proper lighting is critical in creating a reliable, repeatable machine vision application.

Currently, common light sources applied in a machine vision inspection system include halogen, fluorescent, xenon, LED and OLED lamps. Since LEDs have many advantages over other light sources (e.g., long life, low power consumption, fast response time, durability, etc.), LEDs have been widely used in lighting systems for machine vision inspection systems and have gradually replaced other types of light sources, becoming the most commonly utilized technology in machine vision inspection systems.

LED lighting systems are available in numerous form factors including area, line, ring and spot lights. As an example, a line scan application is defined as a machine vision application that utilizes a one-dimensional (1D) line scan camera, and a line light is a lighting system which provides a 1D line of illumination. The most common types of line scan applications are in web manufacturing of various materials (e.g., paper, foil, film, etc.) and in high resolution imaging of larger discrete parts. Such web manufacturing applications typically operate at very high speeds and often operate "24/7" (i.e., 24 hours a day, 7 days a week).

Machine vision systems can only create high quality images if the lighting used to inspect an object clearly illuminates the elements of the object which is being analyzed.

For many applications, the object under inspection is moving at high speed past the camera of the machine vision system, and appropriate lighting apparatus is required in order to obtain the necessary image of the object being inspected. In these situations, LED lights are often "overdriven" by strobe (or pulse) control so as to increase the intensity of the light emitted by the LED light source for a short, defined period of time.

LED lighting manufacturers typically offer LEDs which have a range of different wavelengths for different applications. Aside from the more traditional product offerings of white, red, green, and blue LEDs, ultraviolet (UV) and infrared (IR) LEDs are becoming increasingly popular for performing certain vision inspection tasks. These include use in systems where the materials to be inspected may exhibit fluorescence or where operating personnel must be shielded from bright visible spectrum LED illumination. In other cases, illumination products that combine LEDs to provide multiple wavelengths are being used to reduce the number of inspection stations required in order to inspect multiple aspects of complex objects. For example, a Red-Green-Blue (RGB) LED light head (i.e., LED light source) can produce a dynamic range of colors by independently adjusting the intensity values of the Red, Green, and/or Blue LEDs. This feature allows the operator to dynamically change the color of the light emitted by the LED light head and thus increase the contrast attainable with the machine vision system without deploying multiple light sources (e.g., without providing multiple line lights). Additionally, when all three channels (Red, Green, Blue) are color controlled, the LED light head can produce white light.

In many situations, it is desirable that a line light be capable of operating in single wavelength mode or in multi-wavelength mode (i.e., a mode which produces a combination of different wavelengths). Furthermore, it is frequently also desirable that the line light be capable of adjusting the intensities of the individual LEDs, modifying the strobing functionality of the line light and/or providing the ability to introduce delay signals to the line light (e.g., for synchronizing the line light with cameras).

It is also desirable that the line light utilize a modular design. This modularity provides two important advantages. First, it makes the line light easily serviceable. Among other things, when a given line light module needs to be replaced, that line light module should be easy to remove and replace by a non-technical person. Furthermore, the replacement line light module should then automatically configure itself via software controls to operate in conjunction with the remainder of the line light. Second, modularity makes it possible to provide the line light in varying lengths. To this end, it should be appreciated that the line light should, preferably, be configurable to varying lengths. Different original equipment manufacturers (OEMs) have different length requirements for their line lights, and even individual OEMs have systems with multiple length requirements for their line lights. Providing a modular line light would simplify the production of a line light of variable length.

Further issues relating to the mechanical, optical and electronic aspects of a modular LED line light will hereinafter be discussed.

1. Mechanical Issues

For many machine vision systems, OEMs build highly customized systems for their customers. As a result, the length requirements of their LED line lights vary from system to system. It would be desirable to provide an LED line light that is modular in design, for example a line light capable of having lengths ranging from 100 mm to 5 m, so that the requirements of various customers can be easily met without having to redesign existing line lights. Furthermore, an optimally-designed modular line light system would allow easily replaceable line light modules to be installed in a fast and easy manner.

In many line light applications, the operating environment is harsh. By way of example but not limitation, the line light may be located in an outdoor environment where it may be subjected to significant wind, rain and variations in temperature. By way of further example but not limitation, the line light may be located in an indoor environment where it may be subjected to caustic work environments such as those found on food production lines. In operation, the line light may need to be enclosed in a housing to protect it from such harsh environments. This requirement of a protective housing typically limits the amount of space available for LED driver boards and for fans to cool the LEDs.

Modular line lights also create an issue with respect to the control of individual line light modules within the modular line light. More particularly, these line light modules generally require a unique identification number so that the controller board for the line light can send the correct control signals to each line light module. For line lights operating within a protective enclosure (e.g., in a harsh environment), it is generally difficult to manually assign a unique identification (ID) number to the line light module, due to the difficulty in physically accessing the line light module. Furthermore, there can be issues in the field when some line light modules are replaced or moved to a different location within the modular line light. If the user fails to assign (or reassign) the unique ID numbers for each of the line light modules, the line light will not work as the user expects. Therefore, it would be desirable if auto-enumeration of each line light module in the line light (i.e., auto assignment of each unique ID number for each line light module) is carried out automatically when turning on the line light. In other words, it would be desirable if each line light module has its unique ID number assigned or reassigned to it automatically when turning on the modular LED line light.

In many OEM systems, space is a major constraint. LED line lights need to be designed to minimize space requirements while still ensuring that the reliability and performance of the line light are not compromised.

Furthermore, in keeping with the modular design of the line light, it is desirable to be able to easily replace the LED driver board for a given line light module should the LED driver board fail. Locating the LED driver board within the interior of a line light module generally makes replacement of the LED driver board impractical. By locating the LED driver board for a line light module on the exterior of the line light module, individual LED driver boards can be easily replaced. The LED driver board can be removed and tested simply by removing the LED driver board from the exterior of the line light module, without disrupting any of the internal components of the line light module (e.g., without disrupting alignment of the LED array contained within the line light module). Finally, as noted above, for some applications, it is necessary to enclose the line light in a protective housing to protect it from harsh work environments. This puts a further restriction on the location and size of the LED driver boards for the line light modules.

In addition, the provision of a protective housing about the line light complicates the use of cooling fans to cool the LEDs of the line light. To this end, it would be advantageous for a modular line light to be liquid-cooled (e.g., water-cooled) since it is difficult to utilize cooling fans when the line light is enclosed within a protective housing. In this respect it will be appreciated that even though the LEDs used by the line light may not be of high intensity, some cooling is necessary in order to regulate temperature during operation of the line light.

2. Optical Issues

Some OEM machine vision systems measure objects of varying sizes with the same system. It is, therefore, generally desirable for the "working distance" of the machine vision system to have a relatively wide range, for example, it can be desirable to provide line cameras and line lights that have a working distance across a range of 500 mm. For many commercially available line lights, there is a significant fall-off in the intensity of the line of light at the edges of the line of light emitted from the line light. See FIG. 1. Commercially-available line lights typically exhibit a fall-off in intensity of as much as 30% at the edges of the line of light. To counteract this light fall-off effect, most machine vision systems use line lights that extend beyond the edges of the region being scanned (e.g., that extend beyond the edges of conveyor belts), thereby ensuring that the area under inspection (e.g., the object on the conveyor belt) is relatively uniform. See FIG. 2. However, in many OEM machine vision systems, there is no room to extend the line light beyond the region being scanned, e.g., to extend the line light beyond the width of the conveyor belt. See FIG. 3. In this situation, it is important that the line light provide uniform illumination along the length of the line of light so as to ensure proper inspection of an object.

A further issue arises when lasers are utilized alongside LED lighting in OEM machine vision systems. Due to the simultaneous use of lasers and LED lighting in the machine vision system, "background" light emitted by the line light needs to be minimized so that measurements being taken by the lasers are not distorted. In most "off the shelf" line lights, some stray light will be emitted at the leading and trailing edges of the line of light emitted by the line light. See FIG. 4. In other words, the line of light produced by the line light will not have uniform intensity across its thickness; it will have stray light at the beginning and ends of its thickness dimension. It is important in machine vision systems that stray light emitted by the line lights does not affect the laser data being recorded by the machine vision camera. Thus, it is important that the line light emit an intensity profile which minimizes stray light across its thickness dimension. See FIG. 5.

3. Electronic Issues

As discussed earlier, it is desirable for many OEMs to provide a multi-wavelength line light (i.e., a line light capable of emitting light at multiple wavelengths). The entire line light needs to operate in single wavelength mode or in multi-wavelength mode (i.e., providing light of multiple wavelengths). Adjustment of the intensities of the individual LEDs, strobing functionality and the ability to input delay signals to the line light (e.g., to provide synchronization with line cameras) is required. These line lights need to offer current sensing, voltage sensing, control of the light intensity and control of the strobing functionalities, all within a small form factor and within tight cost constraints.

As will hereinafter be discussed, the present invention addresses these issues.

SUMMARY OF THE INVENTION

The present invention comprises the provision and use of a novel modular LED line light which addresses the foregoing issues.

In one form of the present invention, there is provided a modular LED line light, the modular LED line light comprising:

at least one line light module, the at least one line light module comprising:
- a U-shaped body comprising a base and two opposing side walls extending from the base, the base comprising an interior surface and an exterior surface; and
- at least one LED array disposed on the interior surface of the U-shaped body;

a rail for receiving the at least one line light module, the rail comprising a first surface and a second surface, wherein the first surface is configured to receive the exterior surface of the base of the U-shaped body of the at least one light module; and a cooling tube for receiving a cooling fluid for removing heat from the at least one line light module, the cooling tube being disposed between the exterior surface of the base of the U-shaped body and the first surface of the rail.

In another form of the present invention, there is provided a modular LED line light, the modular LED line light comprising:

a plurality of line light modules, each of the line light modules comprising:
   a U-shaped body comprising a base and two opposing side walls extending from the base, the base comprising an interior surface and an exterior surface; and
   at least one LED array disposed on the interior surface of the U-shaped body;
a rail for receiving the plurality of line light modules, the rail comprising a first surface configured to receive the exterior surfaces of the bases of the U-shaped bodies of the plurality of light modules; and
a common bus bar which delivers electrical power to the plurality of line light modules, wherein the common bus bar comprises two copper rods, wherein each of the copper rods is electrically connected to each of the plurality of line light modules using a clip, wherein each of the clips is longitudinally and rotatably adjustable relative to the copper rod, and wherein the two copper rods are disposed outboard of the side walls of the U-shaped bodies of the plurality of line light modules.

In another form of the present invention, there is provided a modular LED line light, the modular LED line light comprising:

at least one line light module, the at least one line light module comprising:
   a U-shaped body comprising a base and two opposing side walls extending from the base, the base comprising an interior surface and an exterior surface; and
   at least one LED array disposed on the interior surface of the U-shaped body;
   at least one micro lens array for receiving the optical output of the at least one LED array; and
   a macro lens for receiving the optical output of the at least one micro lens array;
   wherein the at least one LED array comprises a plurality of LEDs substantially aligned along a line axis, wherein the at least one micro lens array collimates the light from the at least one LED array perpendicular to the line axis, and further wherein the macro lens collimates the light from the at least one micro lens array parallel to the line axis; and
a rail for receiving the at least one line light module, the rail comprising a surface configured to receive the exterior surface of the base of the U-shaped body of the at least one light module.

In another form of the present invention, there is provided a modular LED line light, the modular LED line light comprising:

a plurality of line light modules, each of the line light modules comprising:
   a U-shaped body comprising a base and two opposing side walls extending from the base, the base comprising an interior surface and an exterior surface; and
   at least one LED array disposed on the interior surface of the U-shaped body;
a rail for receiving the plurality of line light modules, the rail comprising a first surface configured to receive the exterior surfaces of the bases of the U-shaped bodies of the plurality of light modules; and
a controller board for controlling operation of the plurality of line light modules, wherein the controller board automatically assigns a unique ID number to each of the plurality of line light modules when powering on the modular LED line light, and further wherein the controller board assigns a unique ID number to each of the plurality of line light modules in a serial manner, starting at a first line light module and then progressing through each of the remaining line light modules in sequence.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 1-3 are schematic views showing a line light generating a line of light on a conveyor belt;

FIGS. 4 and 5 show how the intensity profile of a line of light may vary across the width of the line of light;

FIGS. 15-19 are schematic views showing the conventional optical components of a conventional LED-based line light;

FIGS. 20 and 21 are schematic views showing how the present invention uses a macro lens with a conically-shaped front face and a cylindrically-shaped back face to provide an increased "depth of field" for the line light;

FIGS. 22-24 are schematic views showing how light collimation and light intensity need to be balanced to achieve a near-uniform intensity profile;

FIGS. 25 and 26 are schematic views showing how a micro lens array/macro lens can be configured in different manners so as to yield different results;

DETAILED DESCRIPTION OF THE PREFERRED EMBODIMENTS

The present invention comprises the provision and use of a novel modular LED line light.

1. General Overview

Figure 1:
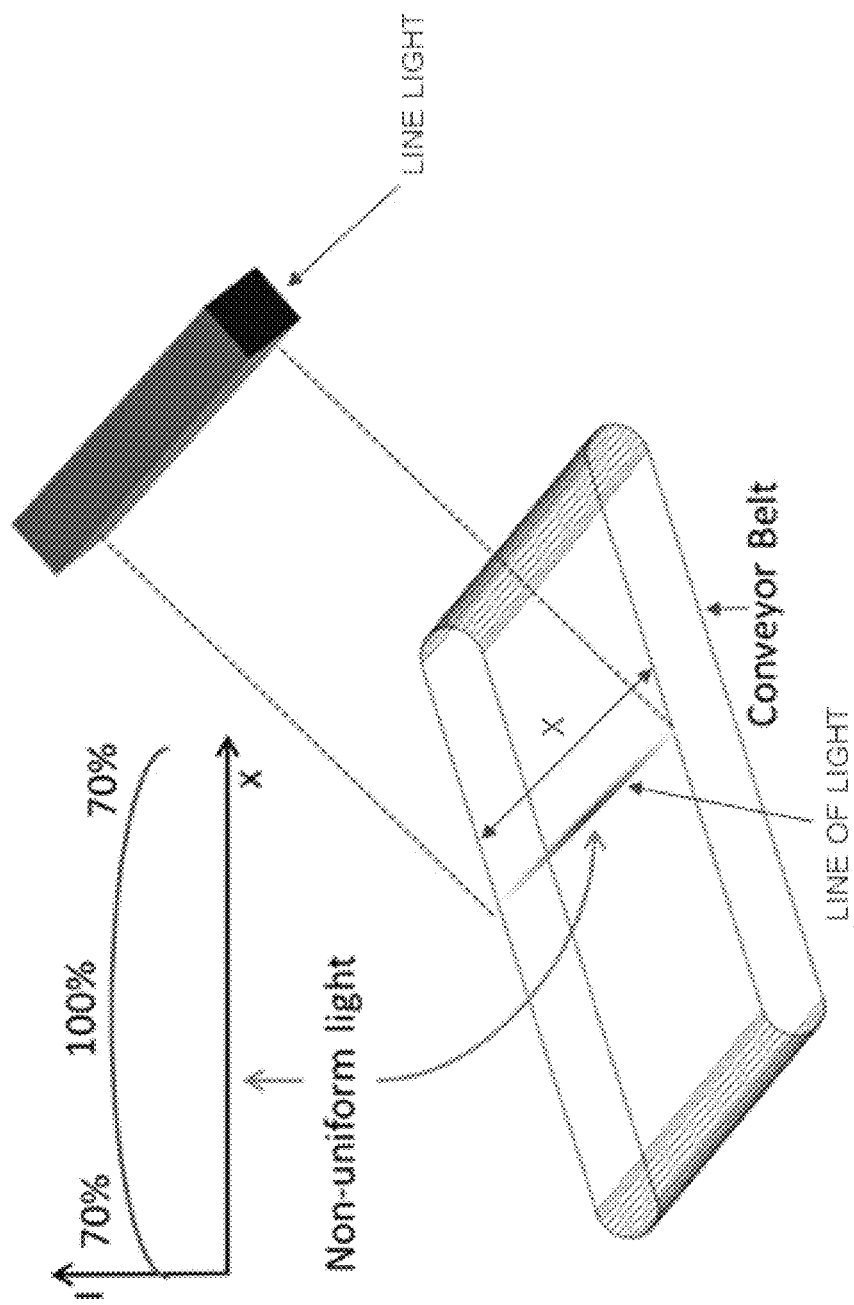
Figure 6:
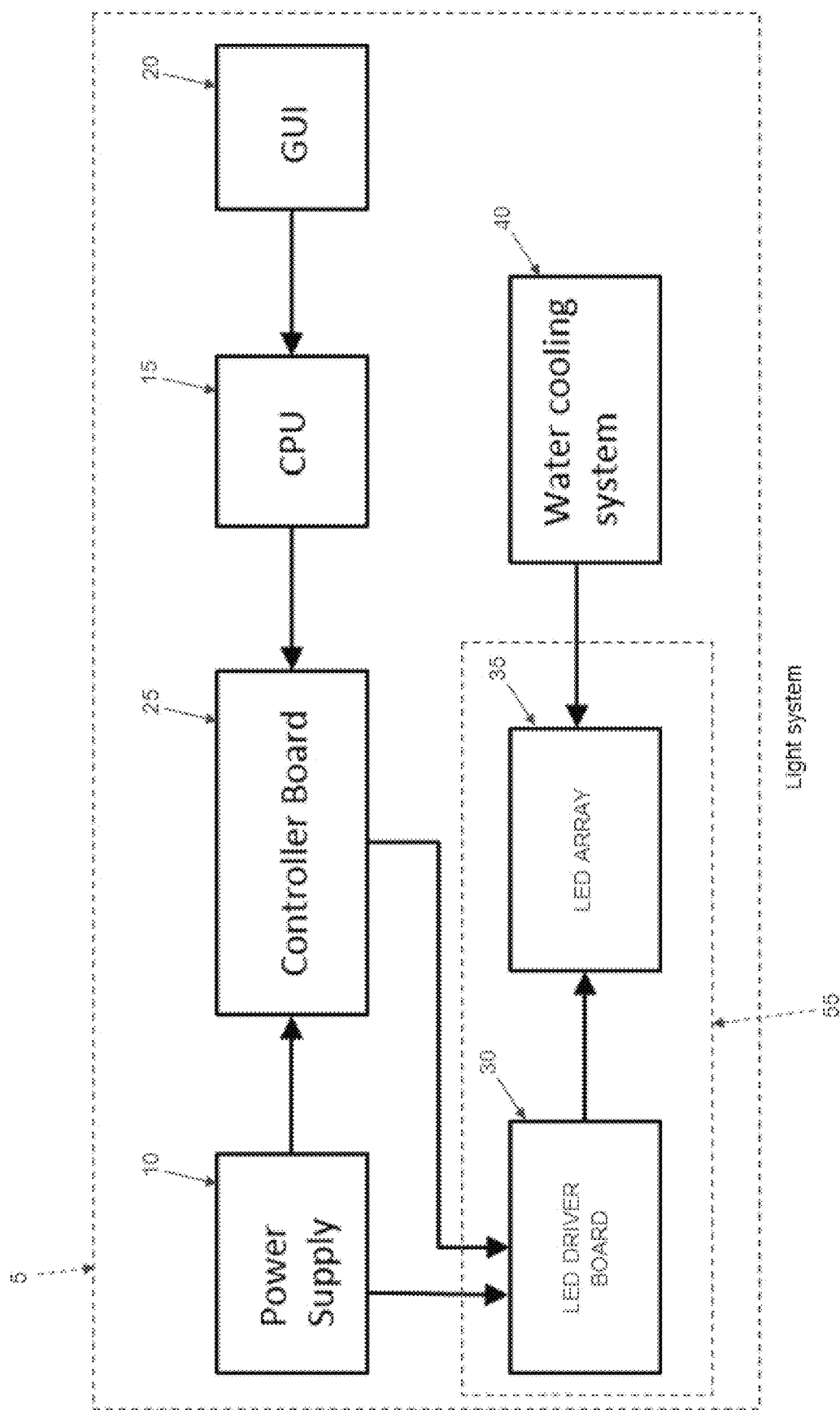
FIG. 6 is a schematic view showing the major components of a novel modular LED line light formed in accordance with the present invention.

In accordance with the present invention, there is provided a novel modular LED line light 5 (see FIG. 6) which generally comprises a power supply 10, a CPU 15, a graphic user interface (GUI) 20, a controller board 25, at least one LED driver board 30, at least one LED array 35 (comprising a plurality of LEDs arranged in a linear configuration, at least when incorporated in a line light) and a liquid cooling system 40 (e.g., a water cooling system). Power supply 10, CPU 15 and GUI 20 can be specifically designed for modular LED line light 5, or the line light can be controlled using general purpose hardware and software elements provided by an OEM system. Power supply 10 is typically a 24V, 30V or 48V DC power supply that provides power to both controller board 25 and LED driver board 30 (which in turn provides power to LED array 35). GUI 20 allows the user to control LED array 35 through customized software of the sort which will be apparent to those skilled in the art in view of the present disclosure. Signals can be passed from GUI 20 to CPU 15 to controller board 25 via electrical or optical signals. At controller board 25, the signals from GUI 20 are processed into data strings and transferred to LED driver board 30, e.g., via Ethernet cable. LED driver board 30 receives the data signals from controller board 25, and receives power from power supply 10, for operating LED array 35.

Figure 8:
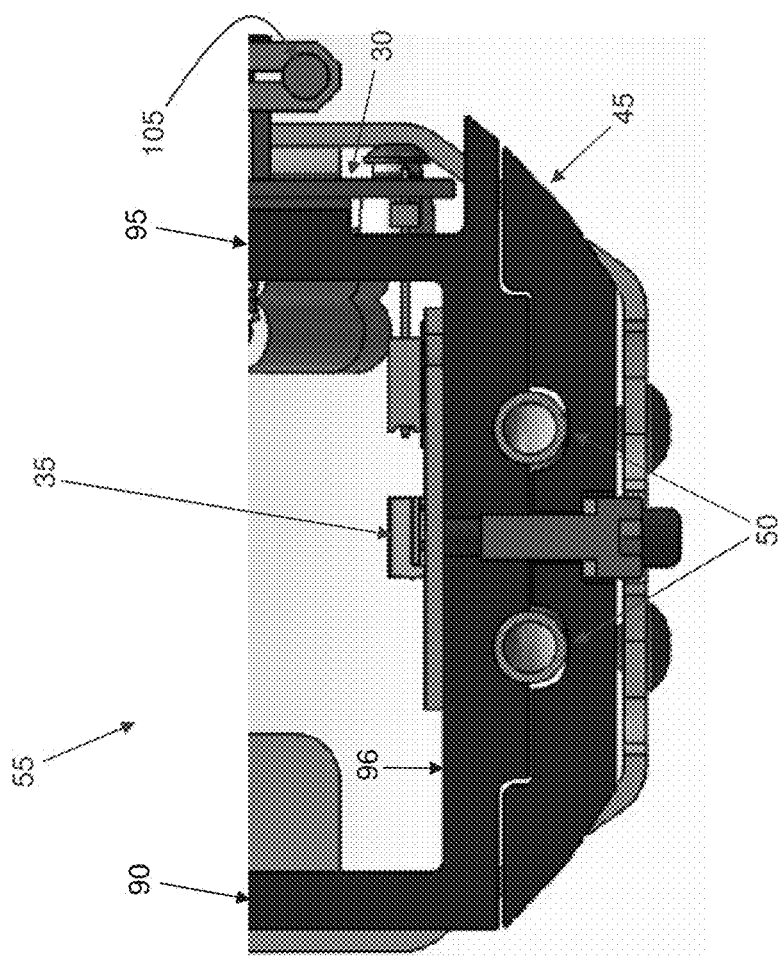
FIGS. 7 and 8 are schematic views showing how line light modules are mounted to a mounting rail.
Figure 7:
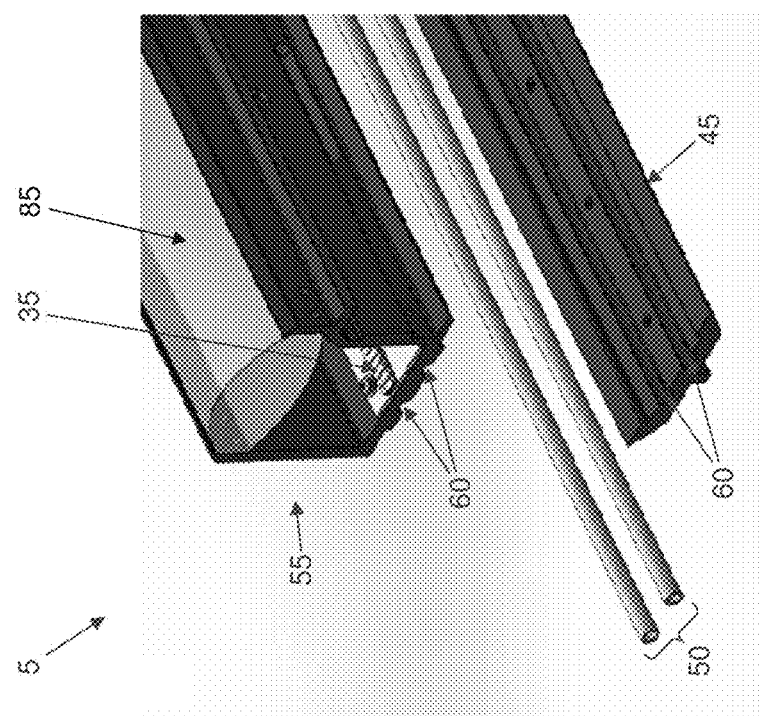

Looking next at FIGS. 7 and 8, there is shown various components of the present invention. More particularly, each modular LED line light 5 comprises a mounting rail 45, a U-shaped cooling tube 50 and one or more line light modules 55 (note that in FIG. 7, only the two linear legs of U-shaped cooling tube 50 are shown and, for clarity of illustration, only one line light module 55 is shown). As will hereinafter be discussed, a plurality of line light modules 55 can be arranged in end-to-end relation so as to together form a complete modular LED line light 5 which produces a singular light pattern (i.e., a single line of light). Mounting rail 45 is typically made from aluminum and U-shaped cooling tube 50 is typically made of stainless steel. The top side of mounting rail 45, and the bottom sides of each of the line light modules 55, have recesses 60 formed therein (preferably semi-circular in cross-section) such that U-shaped cooling tube 50 can be received therein and sit in close contact with mounting rail 45 and the individual line light modules 55, thereby maximizing thermal transfer from the LEDs in LED array 35 to the cooling liquid contained within U-shaped cooling tube 50. During operation of modular LED line light 5, cooling liquid is passed through U-shaped cooling tube 50 to remove heat from novel modular LED line light 5 (which is generated by operation of the LED array(s) 35 in line light module(s) 55, see below). This design ensures that if any leaks occur in U-shaped cooling tube 50, such leaks occur outside of the individual line light modules 55.

For each application, mounting rail 45 and U-shaped cooling tube 50 are manufactured specifically to the length of the line light required. In other words, if a 2 meter line light is required, a 2 meter mounting rail 45 is used, with a U-shaped cooling tube 50 running the length of the 2 meter mounting rail. Each of the individual light modules 55 are designed with a pre-set length, for example, 100 mm. Thus, for a 2 meter line light, twenty 100 mm individual light modules 55 would be used, set end-to-end along the length of mounting rail 45.

Figure 9:
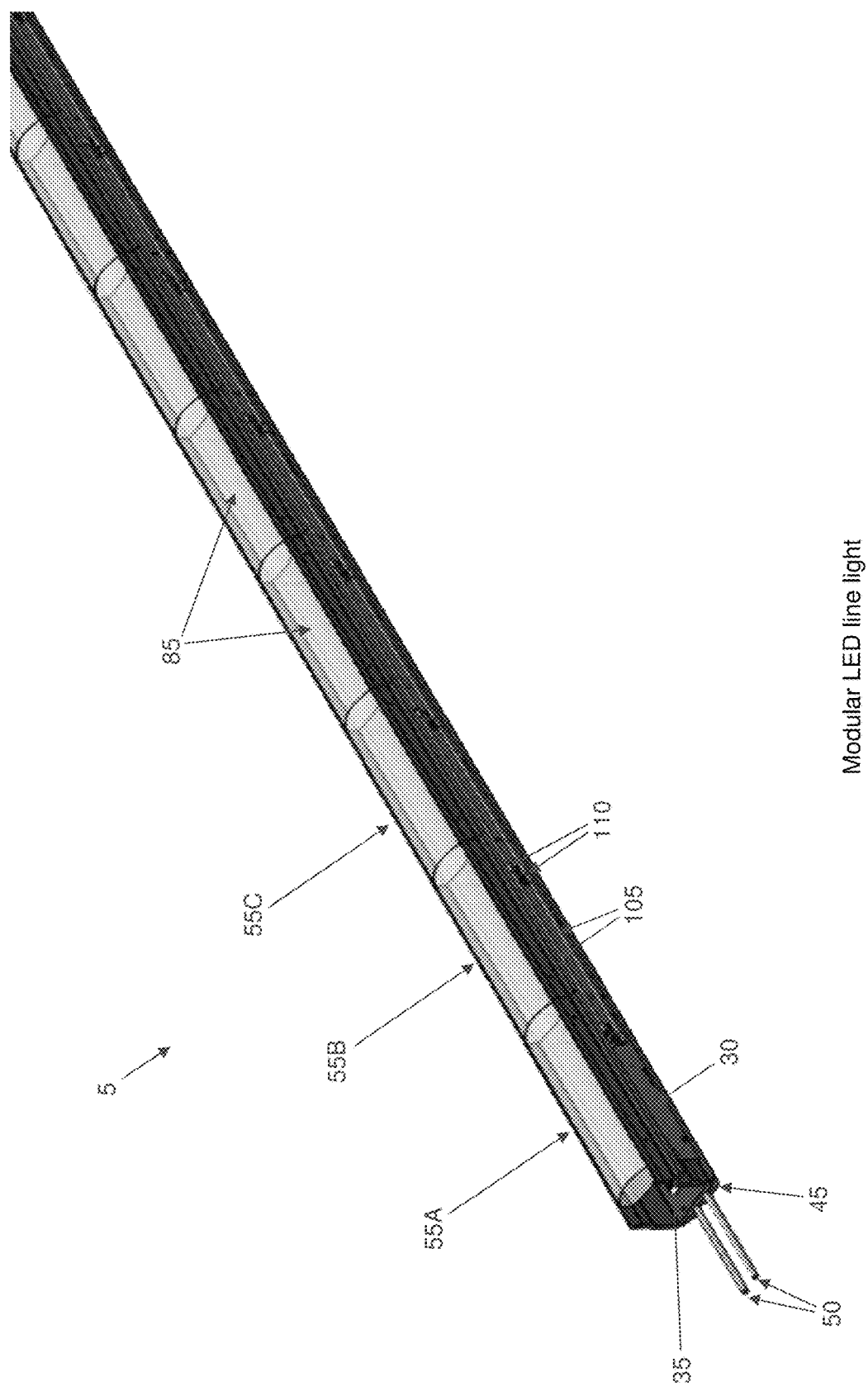
FIG. 9 is a schematic view showing how multiple line light modules are combined in end-to-end fashion so as to form a novel modular LED line light.
Figure 11:
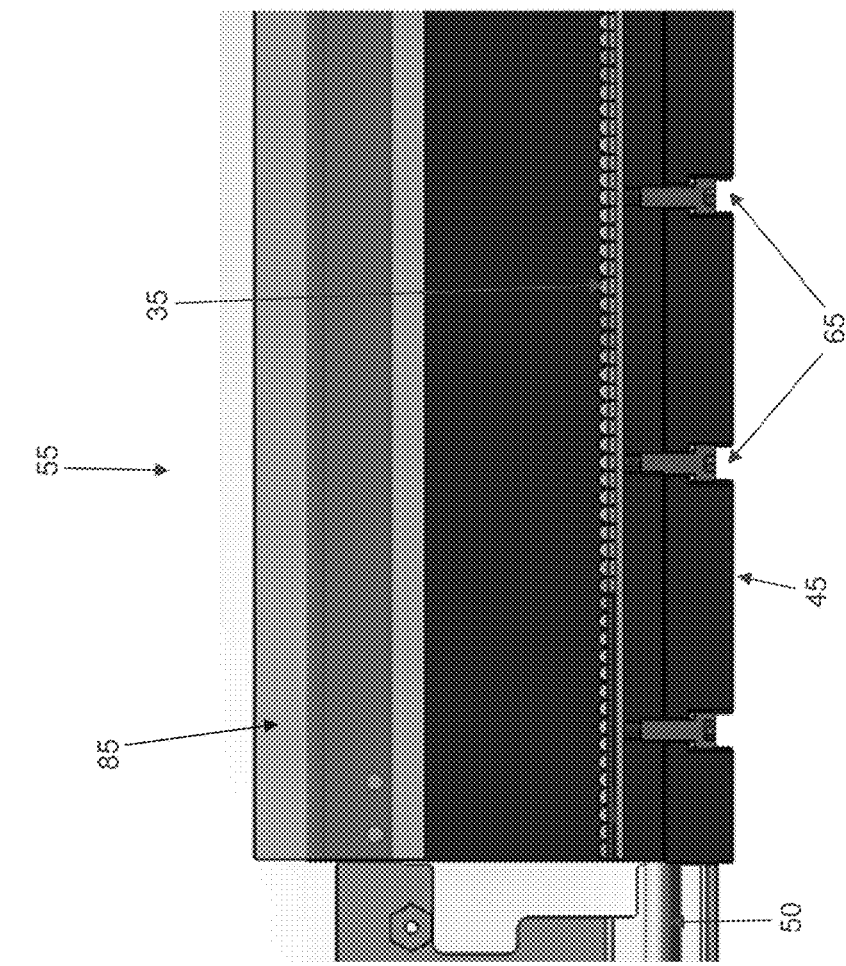
FIGS. 10 and 11 are schematic views showing further details of how line light modules are mounted to a mounting rail.
Figure 10:
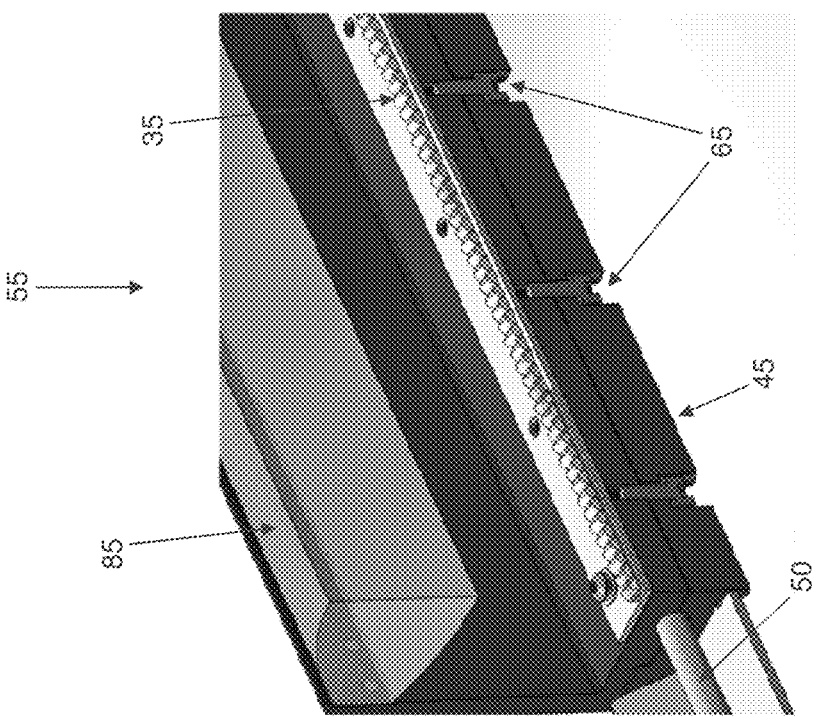

FIG. 9 shows a novel modular LED line light 5 comprising a plurality of individual line light modules 55A, 55B, 55C, etc. arranged in end-to-end fashion on a single mounting rail 45. As will hereinafter be discussed, each individual line light module 55A, 55B, 55C, etc. comprises its own LED driver board 30, LED array 35, micro lens array (see below) and macro lens (see below) so as to constitute a modular assembly. Each of these line light modules is secured to mounting rail 45, and to each other, so as to form novel modular LED line light 5. In other words, novel modular LED line light 5 is made up of a plurality of individual line light modules 55, with each individual line light module constituting its own self-contained unit comprising an LED driver board 30, LED array 35, micro lens array (see below) and macro lens (see below). Each of the individual line light modules 55 are mounted to mounting rail 45 and to adjacent individual line light modules. Together, the LED arrays 35 of line light modules 55A, 55B, 55C, etc. form a line of light (which is tailored by the micro lens arrays and the macro lenses of each individual line light module, as will hereinafter be discussed). The individual line light modules 55A, 55B, 55C, etc. are attached to mounting rail 45 via screws 65 (see FIGS. 10 and 11). The individual line light modules 55A, 55B, 55C, etc. are rigidly held to one another by stainless steel brackets 70 and screws 75 (see FIG. 12).

As discussed above, and looking now at FIG. 8, each of the individual line light modules 55 comprises a plurality of lenses, i.e., a plurality of micro lenses arranged in a micro lens array 80 (with one micro lens of micro lens array 80 being disposed over each LED of LED array 35) and a macro lens 85 (with one macro lens 85 being provided for each line light module 55). Micro lens array 80 is attached directly to LED array 35 so as to tailor the light coming off each of the LEDs of LED array 35. Macro lens 85 slides between the sidewalls 90, 95 of a line light module 55 via a press fit. Sidewalls 90, 95 of a line light module 55 are connected together by a base 96, whereby to collectively form a U-shaped body 97. Base 96 sits atop mounting rail 45. The aforementioned recesses 60 are formed in base 96 and mounting rail 45 so as to receive U-shaped cooling tube 50 therebetween. LED arrays 35 are mounted to the upper surface of base 96. The LED driver board 30 for each line light module 55 is located on the outside of sidewall 95 of the line light module. See FIGS. 13 and 14. Mounting LED driver board 30 exterior to U-shaped body 97 makes LED driver board 30 readily available for servicing and, by spacing LED driver board 30 from LED array 35, helps reduce the footprint of each line light module 55.

The following sections discuss various additional aspects of the present invention in further detail.

2. Optical Aspects

For certain industrial applications, line lights need to work across a wide range of working distances, for example, from 500 mm to 1500 mm.

LEDs typically have wide emission angles (see FIG. 15). In a conventional line light, a micro lens array (FIG. 16) and a cylindrical macro lens (FIG. 17) produce a low divergence beam at the desired working distance (see FIG. 18). However, line lights using a micro lens array in combination with a cylindrical macro lens typically have a relatively short "depth of field".

To work at a wide range of working distances (e.g., from 500 mm to 1500 mm), a line light needs to have a much wider "depth of field" than a conventional line light. For the purposes of the present invention, "depth of field" is considered to be the distance between the nearest object and the furthest object giving a focused image.

To widen the depth of field, the aperture size of the line light needs to be increased. However, utilizing a conventional cylindrical macro lens in the line light with an increased aperture size can result in poorly collimated light. See FIG. 19. To solve this issue, the light entering the macro lens needs to be redirected as it passes through the macro lens so as to produce a more collimated light output profile. To ensure all light exiting the macro lens is collimated, a macro lens (i.e., macro lens 85) having a conically-shaped front face 98 (FIG. 20) and a cylindrically-shaped back face 99 is used with the present invention (see FIG. 21).

It is important to note that there is a careful balance between (i) how much light is collimated versus (ii) the uniformity required for the intensity of the line of light. More particularly, a conventional line light typically produces non-uniform line intensity across the length of the line of light (see FIG. 22). By using a micro lens array 80 that collimates the line of light too much, the resultant line of light exiting the line light can also result in "hot spots" along the line of light. See FIG. 23. Thus, there is a balance between the amount of collimation that can be achieved versus the uniformity of the intensity of the line of light which can be achieved. See FIG. 24. By optimizing the design of micro lens array 80, the design of macro lens 85, and the aperture size of the line light, the desired, collimated uniform intensity line of light can be produced for the desired wide working distance.

In order to increase the uniformity of the intensity of light along the length of the line of light, the emission angle of the LEDs in LED array 35 must be lowered by further collimating the light through a micro lens array 80 of selected design. In a conventional line light, the various lens components (i.e., the micro lenses of micro lens array 80 and the macro lens 85) are typically designed to collimate the light parallel to the line of LED array(s) 35 used in the line light. See FIG. 25. The light is not collimated across the width of the line of light. In the modular LED line light 5 of the present invention, micro lens array 80 collimates the light perpendicular to the line of LED array(s) 35 and macro lens 85 collimates the light along the length of the line of LED array(s) 35. See FIG. 26. Collimation across both axes (perpendicular to the line of LED array(s) 35 and parallel to the line of LED array(s) 35), coupled with the custom lens designs of micro lens array 80 and macro lens 85, also reduces the background light emitted from the line of light (i.e., the width of the line of light is defined by sharper edges).

3. Electronic Aspects

The electronic system of novel modular LED line light 5 generally comprises a power distribution system, a control system and an LED driver board. Each of these will hereinafter be discussed in further detail.

A. Power Distribution System

Typically, in LED-based lighting systems, charge capacitors are used to build up current so that lower input power levels can be utilized. For example, if the LED array(s) 35 require(s) 2 A of current, then a current of 1 A can be directed to LED driver board 30 and stored in charge capacitors on LED driver board 30 until the capacitors reach the requisite 2 A. The required current of 2 A is then released to LED array 35 by LED driver board 30. However, such charge capacitors can add considerably to the cost of the system and can increase the size of the system. On the other hand, if charge capacitors are omitted, then the input current needs to match the current actually required by LED array 35. However, high voltage power supplies are generally expensive. In addition to the foregoing, in many OEM systems, the footprint available for the power supply is limited and traditional cabling solutions require a lot of space for cabling, crimping, screws, etc., while also adding significantly to the cost of the system. These types of systems also tend to suffer from aggregated voltage drops along the length of the line light such that, at the far end of the line light, there may be an excessive voltage drop resulting in uneven light intensity profiles along the length of the line of light. Compensating for this problem with more current may not be possible due to the voltage limits on electronic devices. Therefore, it is desirable to have a high current power distribution method that is relatively inexpensive and is adaptable to limited spaces.

Figure 27:
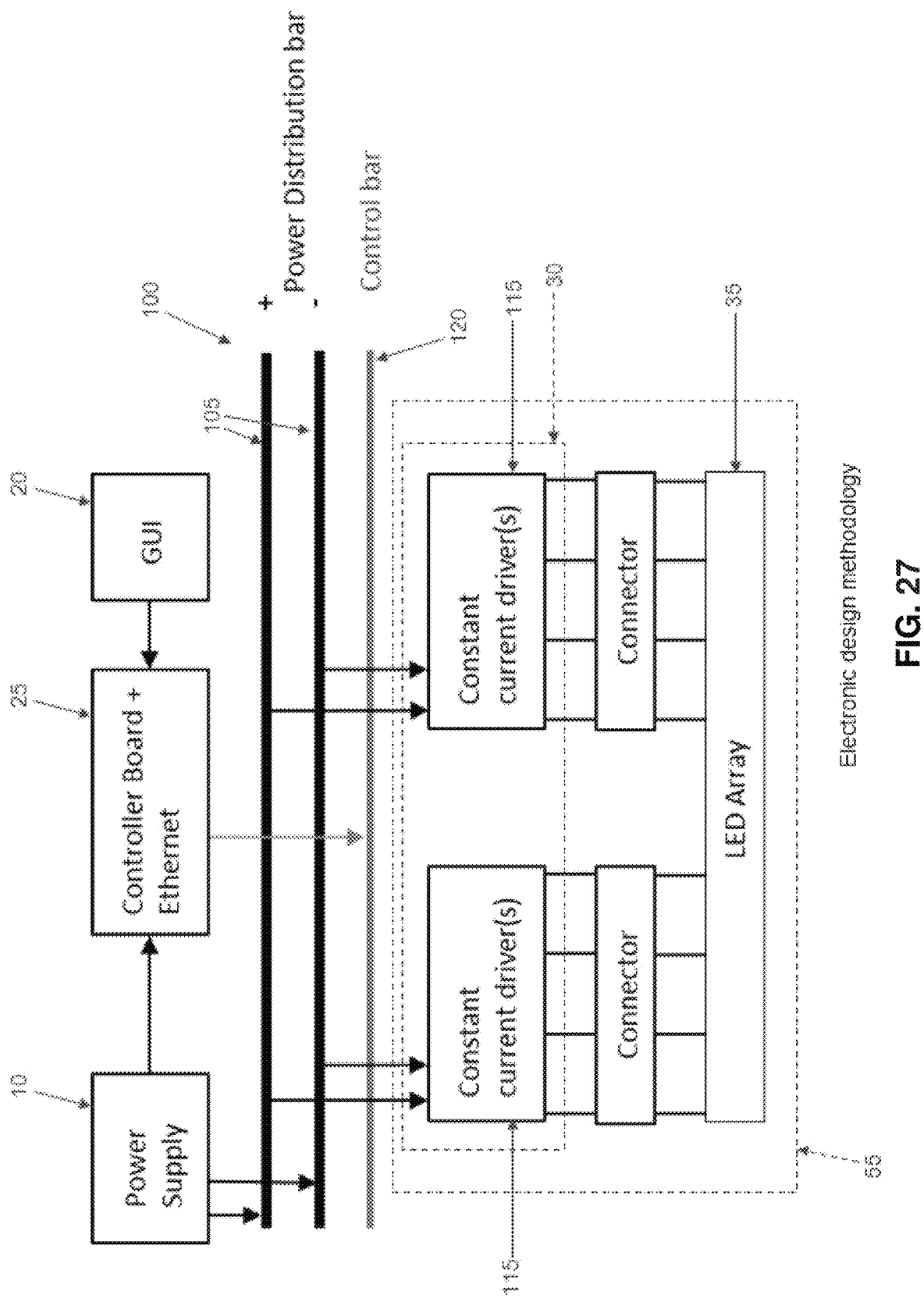
FIG. 27 is a schematic view showing further details of how the LED driver board of a line light module can be driven in accordance with the present invention.
Figure 28:
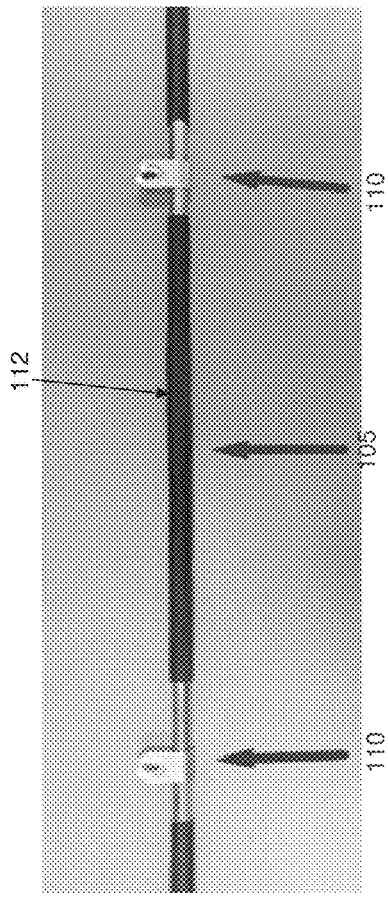
FIGS. 28 and 29 are schematic views showing novel ways for delivering power to a line light module.
Figure 29:
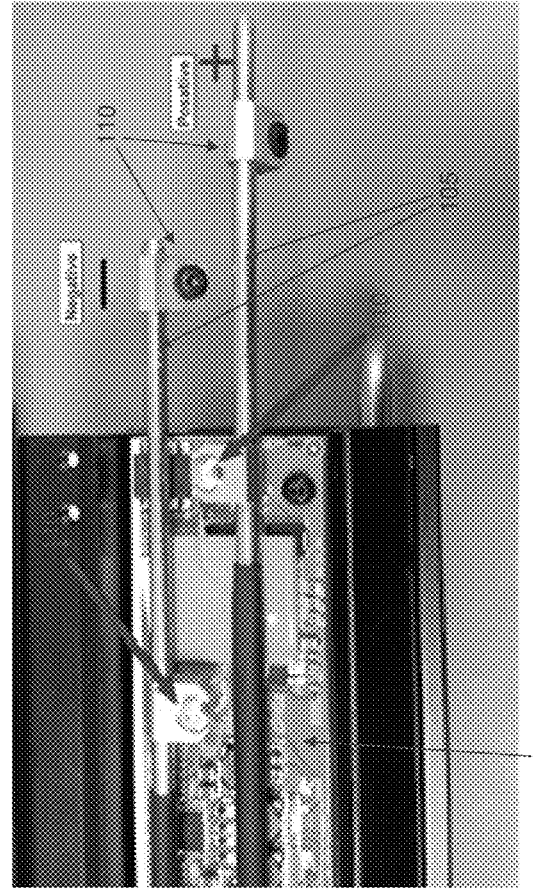

With the present invention, power is distributed from power supply 10 to LED driver board 30 using a cost-effective bus bar 100. See FIG. 27. Bus bar 100 preferably comprises cost-effective copper rods 105 which offer higher conductivity per meter than alternative materials and have the best cross-section for electrical transfer efficiency. Copper rods 105 are commercially available in a variety of thicknesses and can be easily cut to any length required, so they are highly suitable for use in modular systems (which may have varying lengths) and for use in systems which have a variety of different power requirements. Since each copper rod 105 is a single continuous element, there are no interconnects along the length of the copper rod which could cause significant voltage drops along the length of the copper rod. Custom-designed, cost-effective clips 110 (FIGS. 28 and 29) are preferably used to distribute power off copper rods 105 of bus bar 100 to LED driver board 30. Clips 110 can be used wherever they are needed, using as many as needed. Preferably, at least one insulating sleeve 112 (FIG. 28) is disposed on a copper rod 105 between two clips 110. Significantly, copper rods 105 and clips 110 can carry large currents.

B. Control System

Figure 12:
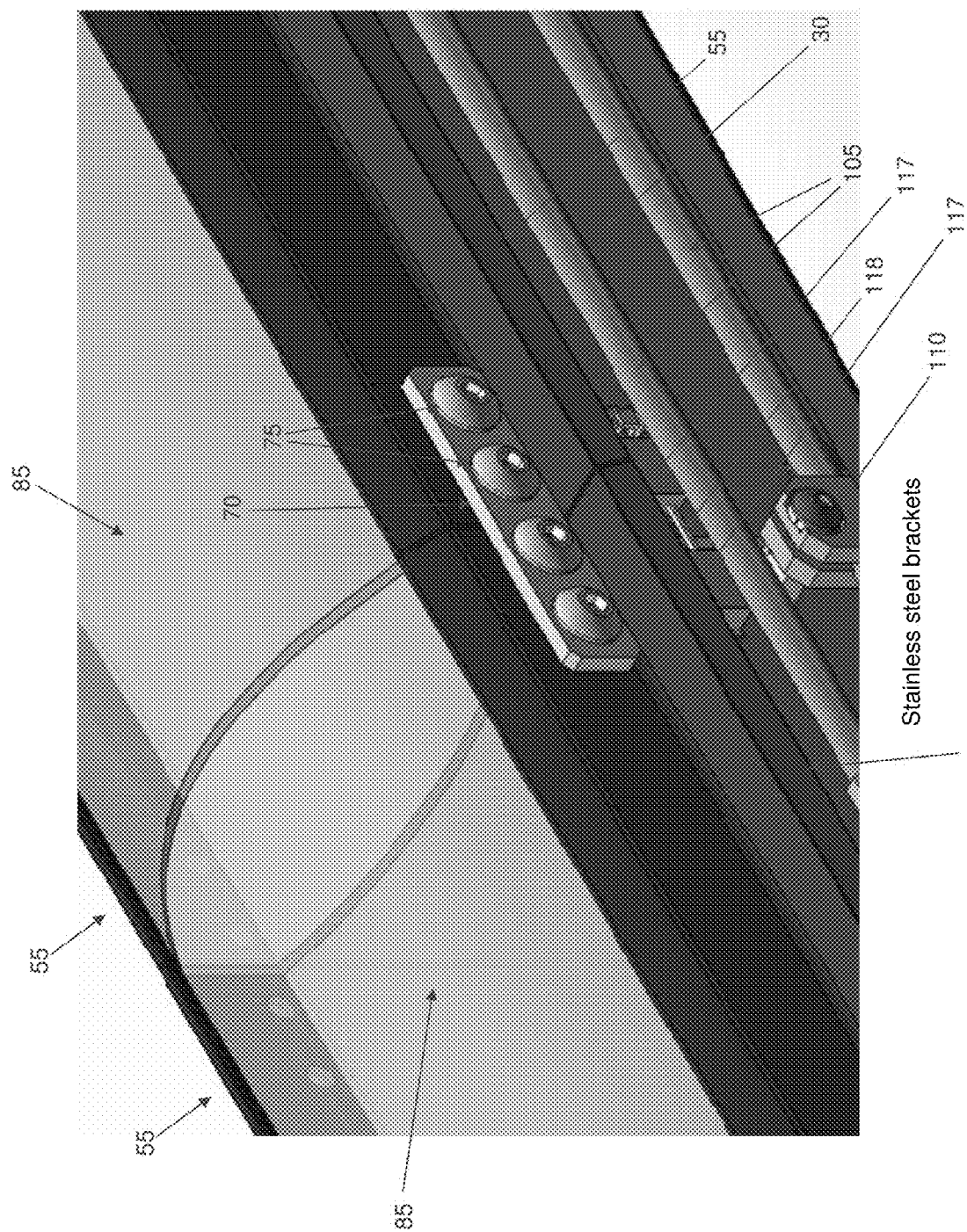
FIG. 12 is a schematic view showing how two adjacent line light modules are mechanically connected to one another.
Figure 13:
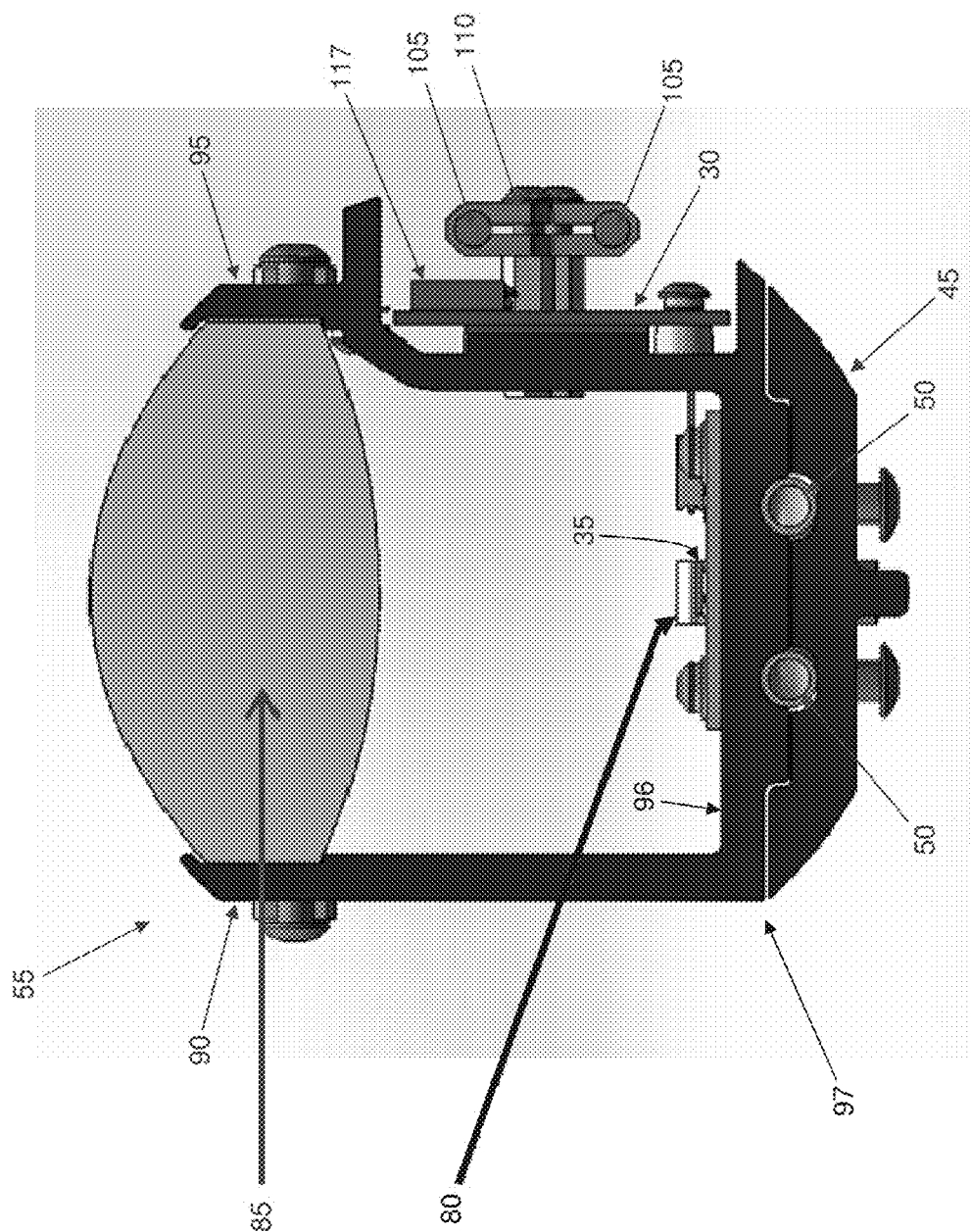
FIG. 13 is a schematic view showing a line light module in end view.
Figure 14:
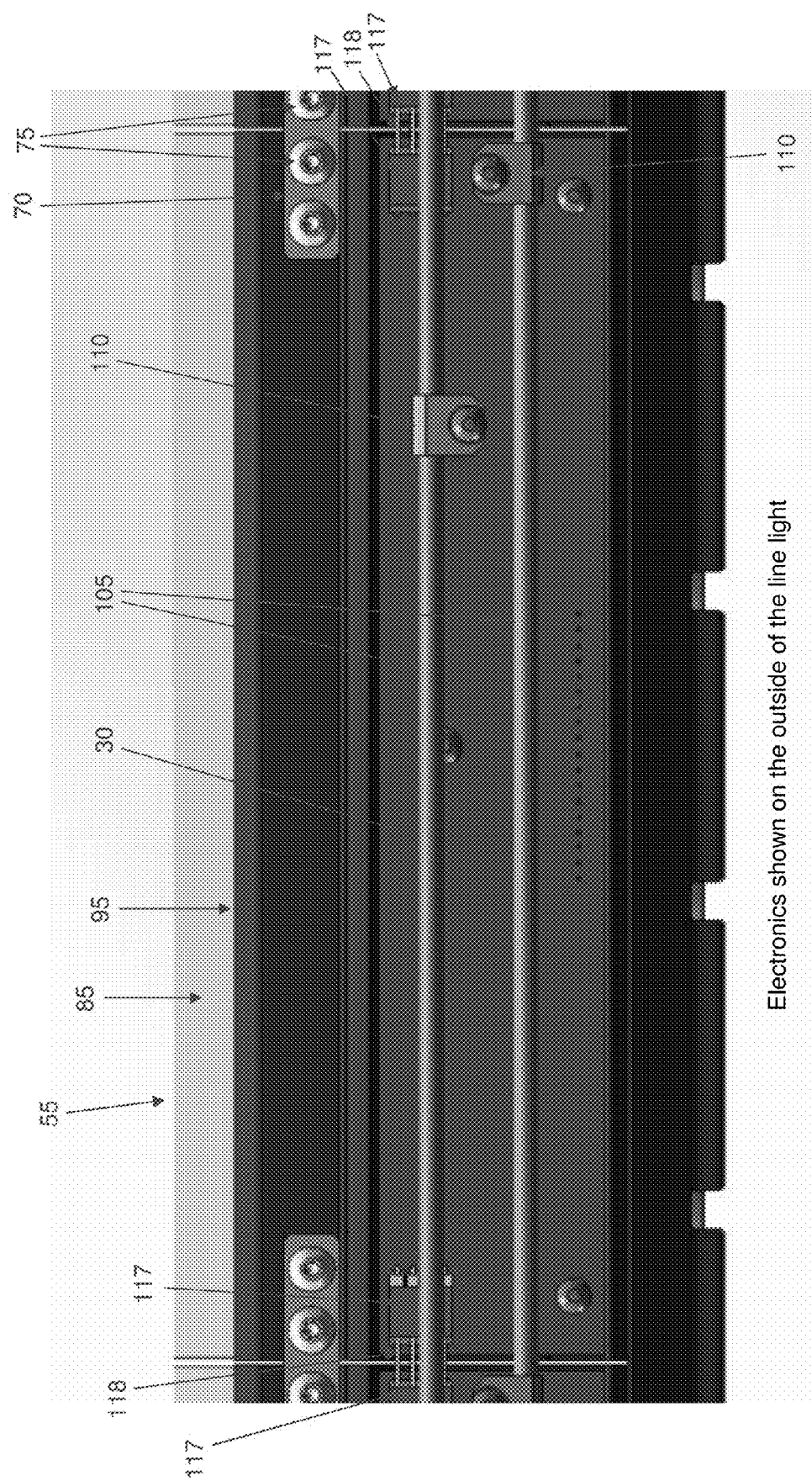
FIG. 14 is a schematic view showing the outside of a line light module mounted between adjacent line light modules.

LED driver board 30 is controlled by a 4-channel control system whose lines run the length of the LED driver boards. The interface used to connect the control system into constant current drivers 115 (FIG. 27) of LED driver board 30 use a CAN-BUS communication protocol. LED driver board 30 is designed so that the CAN-BUS runs from one LED driver board 30 to an adjacent LED driver board 30 along the length of modular LED line light 5, extending from one line light module 55 to the adjacent line light module 55. If an individual line light module 55 is removed and replaced with a new line light module 55, the new line light module 55 can be easily connected into the CAN-BUS. The CAN-BUS is used to send the data instructions to constant current drivers 115 of LED driver board 30 so as to control operation of the LED array 35 of that line light module 55. Individual line light modules 55 are connected together via 4-pin right angle socket connectors 117 (FIGS. 12, 13 and 14). The four pins of the 4-pin right angle socket connectors 117 carry the CAN-BUS signals (HIGH and LOW), a strobe signal and a ground pin. This methodology has a number of advantages. First, it allows for a significant degree of misalignment between line light modules 55 that are assembled together, making efficient electrical connection between the line light modules 55 repeatable and easy to achieve. Second, individual line light modules 55 can be easily removed from the novel modular LED line light 5 (e.g., for replacement). The user simply removes the 4-pin header 118 (FIGS. 12 and 14)

bridging two adjacent 4-pin right angle socket connectors 117 to break the electrical connection between adjacent line light modules 55.

Using this electronic design, the strobe line can be used as a dual use line. First, it allows for a significant degree of misalignment between assembled line light modules 55, making efficient electrical connections repeatable and easy to achieve. Second, the strobe line is used for auto-enumeration of the individual line light modules 55. More particularly, software is used to assign a unique ID to each line light module 55 using the strobe line. In order for modular LED line light 5 to function correctly, each line light module 55 in the modular LED line light 5 needs to be given a unique ID number so that the correct power and/or control signals can be sent to the LED array 35 of that line light module 55. If modular LED line light 5 has no unique ID numbers for its individual line light modules 55, undesired effects can occur. For example, if a user moves the line light modules 55 around within a modular LED line light 5, or if old line light modules 55 are replaced with new line light modules 55, the new line light modules 55 might not turn on or they could emit an unwanted power, spectral or strobe profile.

One method to provide each line light module 55 with a unique ID is to have a physical button located on each line light module 55 which, when pressed, assigns a unique ID number to that line light module 55. However, due to space constraints and mechanical design restrictions (e.g., the modular LED line light 5 may comprise a protective outer housing which can make it impractical to physically access the line light modules 55), it would be preferable to assign (or reassign) unique IDs to the individual line light modules 55 automatically when a line light module 55 is switched on, or control the ID assignment process via software. The ID assignment process is sometimes also referred to as the "enumeration process".

An auto-enumeration process could, for example, be initiated every time modular LED line light 5 is powered up. Controller board 25 sends an ID number signal to each line light module 55. The ID number signal runs along the strobe line, e.g., control bar 120 (FIG. 27), looking to assign itself to the first available line light module 55. So when the modular line light is first turned on, the first ID number is assigned to the first line light module 55. When this happens, all other line light modules 55 in modular LED line light 5 are immediately reset and the process is repeated. A new ID number is run along control bar 120. The new ID number passes by the first line light module 55 (which now has its own unique ID number) and assigns itself to the second line light module 55. When this happens, all of the other line light modules 55 downstream from the second light module 55 are immediately reset and the enumeration process continues. This process is repeated until each of the line light modules 55 in the modular LED line light 5 have been given a unique ID number.

C. LED Driver Board

In accordance with the present invention, a highly integrated LED driver board 30 is provided that connects directly into its associated LED array 35 (which is typically formed on a substrate) using no wiring. This reduces cost and footprint requirements. Current sensing, voltage sensing, control of intensity and strobing are all carried out on a single power chip wired directly to the integrated circuits (IC's) of LED driver board 30. Each LED driver board 30 consists of two quadrupole constant current driver IC's 115, wherein each quadrupole constant current driver IC 115 has 4 outputs. Each output can control an LED chain of LED array 35. The two quadrupole constant current driver IC's 115 drive 8 chains of LEDs on each line light module.

Figure 30:
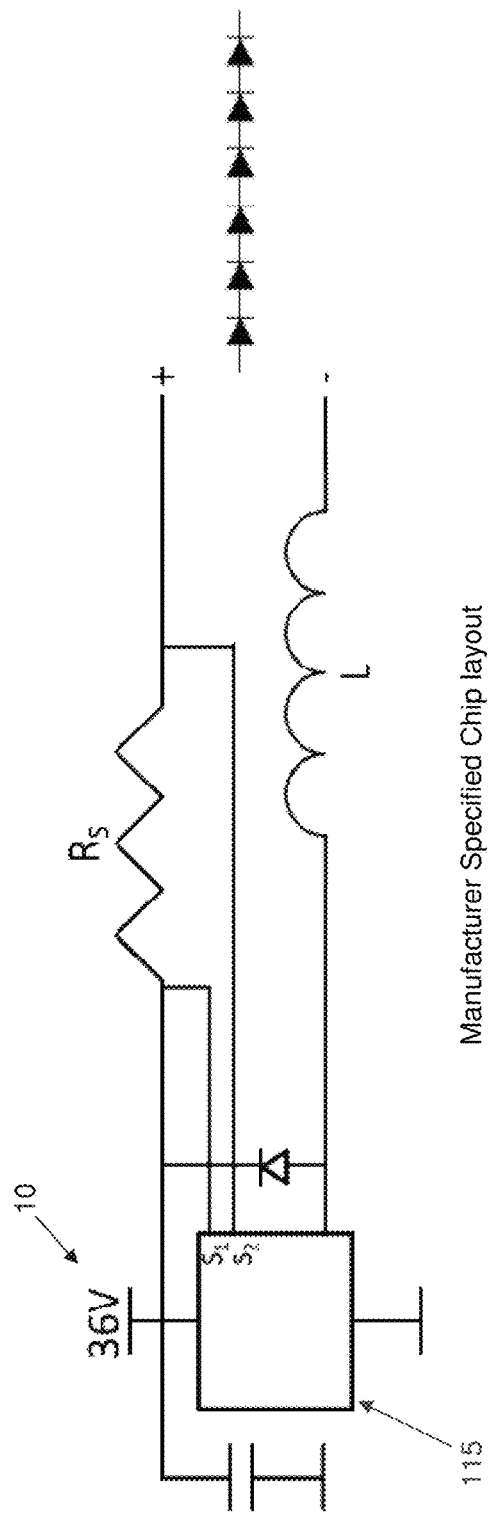
FIGS. 30 and 31 are schematic views showing how the constant current drivers of the LED driver board of a line light module can be driven in accordance with the present invention.

Each quadrupole constant current driver chip 115 has four outlets so it can drive 4 LED strings. FIG. 30 schematically shows one quadrupole constant current driver chip in detail. Following the manufacturer's instructions, these driver chips work by sending current from the external power supply (i.e., power supply 10) through a sense resistor $R_s$ in the driver chip to the LED string, on through an inductor L and down to ground. The circuit is closed for a brief moment. Then, when it is open, the energy that is aggregated in the inductor L is passed around the circuit. The current sensing layout measures the current before and after the sense resistor $R_s$. Utilizing this layout, there is no way to actually relate each current to a specific inductor L. Therefore, it is not possible with this layout to control individual LED strings that may have different duty cycles. Because of the way the drivers 115 are arranged in the circuit, if they are connected together, the current would travel randomly to different inductors L, resulting in a lack of control to individual LED strings.

Figure 31:
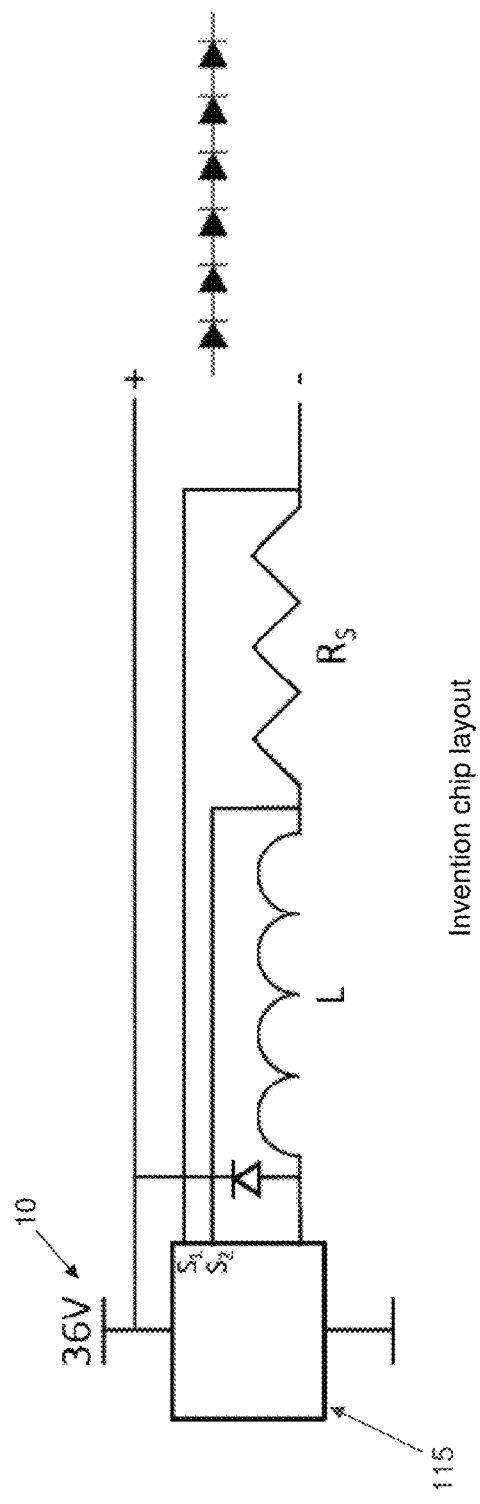

The solution utilized with the present invention is to move the sense resistor $R_s$ to a different location in the layout. See FIG. 31. Utilizing this arrangement, the current is now supplied from a common line and can be split, returned into four independent drivers, hence implementing current sharing into the four chains as is needed. For example, the current can be spread equally into all four LED chains, or a "double current" can be supplied into just two LED chains.

As discussed above, the line light must frequently operate in a harsh environment, and the LED line light is liquid-cooled to eliminate the need for cooling fans. However, if the liquid-cooling fails, the electrical components on LED driver board 30 may be irreparably damaged, resulting in extremely high replacement costs for users utilizing multi-module systems. Modular LED line light 5 therefore needs to be robust enough to withstand liquid-cooling failure.

To this end, LED driver board(s) 30 of the present invention is (are) designed with rooting techniques designed to efficiently remove heat from the devices. A number of solder-filled via's, thermal traces and pads are provided to remove heat from power components such as the inductors L, the constant current drivers 115 and the LEDs of LED array 35 so that heat is dissipated in all dimensions. Thermal traces are commonly used to convey high currents, but in this circuit thermal traces have a dual purpose, in the sense that they are also removing heat from devices. In combination with software control, modular LED line light 5 can operate without any damage to the LED driver board 30 up to 140° C. in the absence of liquid cooling. At 140° C., the software automatically triggers the line light to "gently" shut down, thereby reducing the risk of damage to the entire light system. These features work in combination with a resettable fuse (not shown, but which will be apparent to those skilled in the art in view of the present invention) to ensure a reliable and long life for modular LED line light 5.

A number of features are included to allow testing and debugging to easily take place via visual cues using onboard LEDs. Status LEDs located on the LED driver board 30 flash if a certain part of the circuit is not working correctly. Exemplary measurements include thermal sensing, local voltage verification, ID/strobe line function, status lights, overheating and shorting sensors. As the LED driver board 30 is on the outside of the mechanical housing, this means diagnostics can be completed quickly and easily.

Modular LED Lights Having Non-Linear Configurations

In the foregoing discussion, the present invention is discussed in the context of providing a light engine used for a line scan application (i.e., a light providing a 1D line of illumination). However, it will be obvious to those skilled in the art that the present invention can also be utilized for other applications and/or in other lighting systems having other form factors (e.g., an area light, a ring light, a spot light, etc.).

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A modular LED line light, said modular LED line light comprising:
   at least one line light module, said at least one line light module comprising:
      a U-shaped body comprising a base and two opposing side walls extending from the base, said base comprising an interior surface and an exterior surface; and
      at least one LED array disposed on said interior surface of said U-shaped body;
   a rail for receiving said at least one line light module, said rail comprising a first surface and a second surface, wherein said first surface is configured to receive said exterior surface of said base of said U-shaped body of said at least one light module; and
   a cooling tube for receiving a cooling fluid for removing heat from said at least one line light module, said cooling tube being disposed between said exterior surface of said base of said U-shaped body and said first surface of said rail.

2. A modular LED line light according to claim 1 wherein at least one of said exterior surface of said base of said U-shaped body and said first surface of said rail comprises a recess for receiving said cooling tube.

3. A modular LED line light according to claim 2 wherein said exterior surface of said base of said U-shaped body and said first surface of said rail both comprise a recess for receiving said cooling tube.

4. A modular LED line light according to claim 3 wherein said recess in said exterior surface of said base of said U-shaped body and said recess in said first surface of said rail are both aligned with one another when said at least one light module is received on said rail.

5. A modular LED line light according to claim 1 wherein said cooling tube comprises at least two legs disposed substantially parallel to one another.

6. A modular LED line light according to claim 1 wherein said modular LED line light comprises a plurality of line light modules, and further wherein said rail is configured to receive said plurality of line light modules and said cooling tube is configured to remove heat from said plurality of line light modules.

7. A modular LED line light according to claim 1 wherein said at least one line light module is releasably mounted to said rail.

8. A modular LED line light according to claim 7 wherein said at least one line light module is releasably mounted to said rail using at least one screw.

9. A modular LED line light according to claim 1 wherein said modular LED line light comprises a plurality of line light modules, wherein said rail is configured to receive said plurality of line light modules and said cooling tube is configured to remove heat from said plurality of line light modules, wherein each line light module is secured to said rail, and further wherein each line light module is secured to an adjacent line light module using a connector which extends from that line light module to the adjacent line light module.

10. A modular LED line light according to claim 9 wherein said at least one line light module is secured to said rail using at least one screw, and further wherein said connector is secured to each of the adjacent line light modules using at least one screw.

11. A modular LED line light according to claim 1 wherein said modular LED line light comprises a plurality of line light modules, and further wherein said modular LED line light further comprises a common bus bar which delivers electrical power to said plurality of line light modules.

12. A modular LED line light according to claim 11 wherein said common bus bar comprises two copper rods, and further wherein each of said copper rods is electrically connected to each of said plurality of line light modules.

13. A modular LED line light according to claim 12 wherein each copper rod is connected to each of said line light modules using a clip.

14. A modular LED line light according to claim 13 wherein each of said clips is adjustably mounted to a copper rod.

15. A modular LED line light according to claim 14 wherein each of said clips is longitudinally and rotatably adjustable relative to said copper rod.

16. A modular LED line light according to claim 13 further comprising at least one insulating sleeve disposed on a copper rod between two of said clips.

17. A modular LED line light according to claim 12 wherein said two copper rods are disposed outboard of said side walls of said U-shaped bodies of said plurality of line light modules.

18. A modular LED line light according to claim 11 wherein each of said plurality of line light modules comprises an LED driver board for driving said at least one LED array of that line light module, and further wherein said LED driver board is disposed outboard of said side walls of said U-shaped bodies of said plurality of line light modules.

19. A modular LED line light according to claim 1 wherein said at least one line light module further comprises at least one micro lens array for receiving the optical output of said at least one LED array, and a macro lens for receiving the optical output of said at least one micro lens array.

20. A modular LED line light according to claim 19 wherein said at least one LED array comprises a plurality of LEDs substantially aligned along a line axis, wherein said at least one micro lens array collimates the light from said at least one LED array perpendicular to said line axis, and further wherein said macro lens collimates the light from said at least one micro lens array parallel to said line axis.

21. A modular LED line light according to claim 20 wherein the intensity profile of the light from said at least one LED array is balanced vis-à-vis the collimation provided by said at least one micro lens array and said macro lens so as to provide a near-uniform intensity profile along the length of the beam of light passing through said macro lens.

22. A modular LED line light according to claim 1 wherein said modular LED line light comprises a plurality of line light modules, and further wherein said modular LED line light comprises a controller board for controlling operation of said plurality of line light modules.

23. A modular LED line light according to claim 22 wherein said controller board assigns a unique ID number to each of said plurality of line light modules.

24. A modular LED line light according to claim 23 wherein said controller board automatically assigns a unique ID number to each of said plurality of line light modules when powering on said modular LED line light.

25. A modular LED line light according to claim 23 wherein said controller board assigns a unique ID number to each of said plurality of line light modules in a serial manner, starting at a first line light module and then progressing through each of the remaining line light modules in sequence.

26. A modular LED line light according to claim 23 wherein, when said controller board assigns a unique ID number to a given line light module, the ID numbers of all of the line light modules downstream of the line light module which is currently being assigned its unique ID number are reset in preparation for receiving their own unique ID numbers.

27. A modular LED line light, said modular LED line light comprising:

a plurality of line light modules, each of said line light modules comprising:

a U-shaped body comprising a base and two opposing side walls extending from the base, said base comprising an interior surface and an exterior surface; and at least one LED array disposed on said interior surface of said U-shaped body;

a rail for receiving said plurality of line light modules, said rail comprising a first surface configured to receive said exterior surfaces of said bases of said U-shaped bodies of said plurality of light modules; and a common bus bar which delivers electrical power to said plurality of line light modules, wherein said common bus bar comprises two copper rods, wherein each of said copper rods is electrically connected to each of said plurality of line light modules using a clip, wherein each of said clips is longitudinally and rotatably adjustable relative to said copper rod, and wherein said two copper rods are disposed outboard of said side walls of said U-shaped bodies of said plurality of line light modules.

* * * * *